US010632259B2

(12) United States Patent
Scott et al.

(10) Patent No.: US 10,632,259 B2
(45) Date of Patent: Apr. 28, 2020

(54) MEDICAMENT DELIVERY DEVICE AND ASSEMBLY OF ELECTRONIC DEVICE AND THE MEDICAMENT DELIVERY DEVICE

(71) Applicant: SHL MEDICAL AG, Zug (CH)

(72) Inventors: Daniel Scott, Deerfield Beach, FL (US); Slobodan Stefanov, Deerfield Beach, FL (US); Chun Chu, Taipei (TW)

(73) Assignee: SHL MEDICAL AG, Zug (CH)

( * ) Notice: Subject to any disclaimer, the term of this patent is extended or adjusted under 35 U.S.C. 154(b) by 139 days.

(21) Appl. No.: 15/753,902

(22) PCT Filed: Aug. 9, 2016

(86) PCT No.: PCT/EP2016/068970
§ 371 (c)(1),
(2) Date: Feb. 20, 2018

(87) PCT Pub. No.: WO2017/032590
PCT Pub. Date: Mar. 2, 2017

(65) Prior Publication Data
US 2018/0243504 A1    Aug. 30, 2018

(30) Foreign Application Priority Data
Aug. 26, 2015   (SE) ...................................... 1551104

(51) Int. Cl.
*A61M 5/20*     (2006.01)
*A61M 5/32*     (2006.01)
(Continued)

(52) U.S. Cl.
CPC ...... *A61M 5/2033* (2013.01); *A61M 5/31585* (2013.01); *A61M 5/326* (2013.01);
(Continued)

(58) Field of Classification Search
CPC ............ A61M 5/20; A61M 2005/2013; A61M 2005/208; A61M 5/2466; A61M 5/3243;
(Continued)

(56) References Cited

U.S. PATENT DOCUMENTS 5,658,259 A *  8/1997  Pearson ............... A61M 5/2033
                                              604/136
6,210,369 B1   4/2001  Wilmot et al.
(Continued)

FOREIGN PATENT DOCUMENTS

CN       102099069 A     6/2011
TW       201417853 A     5/2014
(Continued)

OTHER PUBLICATIONS

International Search Report issued in International Application No. PCT/EP2016/068970 dated Nov. 14, 2016.
(Continued)

*Primary Examiner* — Kami A Bosworth
*Assistant Examiner* — Antarius S Daniel
(74) *Attorney, Agent, or Firm* — McDonnell Boehnen Hulbert & Berghoff LLP

(57) ABSTRACT

A medicament delivery device includes a holding unit (5), a driving unit (7) releasably held by the holding unit, an activation unit (6) used to release the driving unit from the holding unit, and an injection unit (8) to be moved by the driving unit. The injection unit includes a hub (85) held by the driving unit, a cannula (86) fixed to the hub and a container (83) slidably connected to the hub. After the driving unit is released, the proximal end of the cannula protrudes out of the activation unit before the distal end of the cannula fluidly communicates with the container. The medicament delivery device is combined with an electronic device in an assembly. When a casing cap of the assembly
(Continued)

is removed, the electronic device or an app in the electronic device or a function of the electronic device is automatically activated to wirelessly communicate with another electronic device.

17 Claims, 20 Drawing Sheets

(51) Int. Cl.
*G16H 20/17* (2018.01)
*H04M 1/21* (2006.01)
*A61M 5/315* (2006.01)
*A61M 5/24* (2006.01)
*H04M 1/18* (2006.01)
*A61M 5/31* (2006.01)
*H04M 1/02* (2006.01)

(52) U.S. Cl.
CPC .............. *G16H 20/17* (2018.01); *H04M 1/21* (2013.01); *A61M 2005/206* (2013.01); *A61M 2005/2013* (2013.01); *A61M 2005/247* (2013.01); *A61M 2005/3103* (2013.01); *A61M 2005/3125* (2013.01); *A61M 2005/3247* (2013.01); *A61M 2205/3553* (2013.01); *A61M 2205/3569* (2013.01); *A61M 2205/3584* (2013.01); *A61M 2205/3592* (2013.01); *A61M 2205/581* (2013.01); *A61M 2209/08* (2013.01); *H04M 1/0202* (2013.01); *H04M 1/185* (2013.01)

(58) Field of Classification Search
CPC .. A61M 2005/3261; A61M 2005/3263; A61M 2005/3267; A61M 5/50; A61M 5/31585; A61M 5/326; A61M 2005/247; A61M 2005/3247; A61M 2205/3553; A61M 2205/3569; A61M 2005/206; A61M 5/2455; H04B 1/3888
See application file for complete search history.

(56) References Cited

U.S. PATENT DOCUMENTS

| | | | |
|---|---|---|---|
| 8,551,054 B2 | 10/2013 | Guillermo | |
| 8,639,288 B1* | 1/2014 | Friedman | A61M 5/20 455/556.1 |
| 9,861,754 B2 | 1/2018 | Holmqvist | |
| 2004/0215151 A1* | 10/2004 | Marshall | A61M 5/2033 604/198 |
| 2005/0171477 A1* | 8/2005 | Rubin | A61M 5/2033 604/156 |
| 2007/0073232 A1* | 3/2007 | Pickhard | A61M 5/2033 604/134 |
| 2008/0306449 A1* | 12/2008 | Kristensen | A61M 5/20 604/192 |
| 2011/0125100 A1 | 5/2011 | Schwirtz et al. | |
| 2012/0220954 A1 | 8/2012 | Cowe | |
| 2013/0035644 A1 | 2/2013 | Giambattista et al. | |
| 2013/0053790 A1* | 2/2013 | Karlsson | A61M 5/2033 604/218 |
| 2013/0211330 A1* | 8/2013 | Pedersen | A61M 5/2033 604/111 |
| 2013/0218093 A1 | 8/2013 | Markussen et al. | |
| 2013/0310757 A1* | 11/2013 | Brereton | A61M 5/31501 604/197 |
| 2015/0174324 A1* | 6/2015 | Wurmbauer | A61M 5/20 604/157 |
| 2015/0273162 A1 | 10/2015 | Holmqvist | |
| 2016/0015901 A1 | 1/2016 | Plumptre | |
| 2016/0051765 A1 | 2/2016 | Morris et al. | |
| 2016/0067411 A1 | 3/2016 | Morris | |
| 2018/0344937 A1 | 12/2018 | Lööf et al. | |

FOREIGN PATENT DOCUMENTS

| | | |
|---|---|---|
| TW | 2014341577 A | 8/2014 |
| TW | 201509458 A | 3/2015 |
| TW | 201509467 A | 3/2015 |
| TW | 201521808 A | 6/2016 |
| WO | 2013032389 A1 | 3/2013 |
| WO | 2013154954 A1 | 10/2013 |
| WO | 2015070340 A1 | 5/2015 |
| WO | WO-2015070340 A1 * | 5/2015 |

OTHER PUBLICATIONS

Search Report issued in Taiwanese Patent Application No. 105126401 dated Apr. 7, 2017.

* cited by examiner

MEDICAMENT DELIVERY DEVICE AND ASSEMBLY OF ELECTRONIC DEVICE AND THE MEDICAMENT DELIVERY DEVICE

CROSS REFERENCE TO RELATED APPLICATIONS

The present application is a U.S. National Phase Application pursuant to 35 U.S.C. § 371 of International Application No. PCT/EP2016/068970 filed Aug. 9, 2016, which claims priority to Swedish Patent Application No. 1551104-1 filed Aug. 26, 2015. The entire disclosure contents of these applications are hereby incorporated by reference into the present application.

FIELD OF THE INVENTION

This invention generally relates to a medicament delivery device, and more particularly to an assembly of the medicament delivery device with an electronic device (such as a cell phone).

BACKGROUND OF THE INVENTION

FIG. 1 is an assembly 9 of an auto-injector 91 and a cell phone 92 disclosed in U.S. Pat. No. 8,639,288 B1. However, the disclosed assembly 9 is difficult to operate. Besides, in known auto-injectors (such as that disclosed in US 2012-0220954 A1), a needle of the auto-injector is in fluid communication with a medicament container. Alternatively, the needle is arranged to penetrate a septum of the medicament container prior to penetrating a user's tissue. Such prior art auto-injectors will result in medicament leakage outside the user's body so that the user will not obtain a sufficient dose of medicament. In other words, the disclosed auto-injector is difficult to control to get an accurate dose.

SUMMARY OF THE INVENTION

Accordingly, this invention relates to a medicament delivery device and an assembly of an electronic device with the medicament delivery device, with the intention to substantially obviate one or more of the problems encountered in the prior art.

One object of this invention is to provide an assembly of an electronic device and a medicament delivery device, which assembly is easy to operate.

Another object of this invention is to provide a medicament delivery device which does not leak medicament outside a user's body.

Yet another object of this invention is to provide a medicament delivery device which injects an accurate dose of medicament into a user's body.

These objects are achieved by a medicament delivery device as defined by claim 1 and an assembly of an electronic device with the medicament delivery device as defined by claim 17. The dependent claims define preferred or advantageous embodiments of the medicament delivery device and the assembly of the electronic device with the medicament delivery device.

Additional features and advantages of the invention will be set forth in the following description, and will be apparent from the description, or may be learned by practice of the invention. The objectives and advantages of the invention will be realized and attained by the structure as particularly set forth in the written description and in the claims, as well as illustrated in the appended drawings.

To achieve these and other advantages, according to the purpose of this invention as embodied and broadly described, a medicament delivery device comprises: a holding unit; a driving unit releasably connected to the holding unit; an activation unit slidable relative to the holding unit and arranged to release the driving unit from the holding unit; and an injection unit configured to be moved by the driving unit. The injection unit includes: a hub releasably connected to the driving unit; a cannula fixed to the hub; and a container releasably connected to the hub and slidable relative to the hub, the container comprises a septum; wherein before the driving unit is released from the holding unit, a proximal end of the cannula is concealed in the activation unit and a distal end of the cannula is outside the container; and wherein after the driving unit is released from the holding unit, the proximal end of the cannula protrudes out of the activation unit before the distal end of the cannula penetrates the septum. Thus, the hub is configured to be moved by the drive unit from a first position, in which a proximal end of the cannula is concealed in the activation unit and a distal end of the cannula is outside the container, to a second position, in which the proximal end of the cannula protrudes from the activation unit and the distal end of the cannula is outside the container and wherein the container is configured to be moved from an initial position, in which the container moves with the hub from the first to the second position, to a final position relative to the hub, in which the container is released from the hub such that the septum is penetrated by the distal end of the cannula. I.e. the driving unit is configured to displace the hub from a first position to a second position in relation to the holding unit and to subsequently displace the container from an initial position to a final position in relation to the hub when the driving unit is released such that when the hub is in the first position and the container is in the initial position, the proximal end of the cannula is concealed in the activation unit and the distal end of the cannula is outside the septum; and such that when the hub is in the second position and the container is in the initial position, the proximal end of the cannula is protruding from the activation unit and the distal end of the cannula is outside the septum of the container; and such that when the hub is in the second position and the container is in the final position, the proximal end of the cannula is protruded from the activation unit and the distal end of the cannula is penetrated in the septum of the container.

Moreover, after the driving unit is released from the holding unit by the activation unit, the hub together with the container is moved by the driving unit. The hub is stopped by the activation unit before the container is stopped so as to allow the distal end of the cannula going into the container. Thus, the hub is configured to be stopped by the activation unit when the hub reaches the second position.

It is another preferred feature that the hub has a tongue and the container has a body, a head and a neck connecting the head to the body. The tongue is engaged with the neck to lock and stop the container when the container reaches the final position. Additionally, the activation unit is formed with a first window which is aligned with the tongue to allow the head sliding over the tongue.

Furthermore, the activation unit includes a needle shield formed with the first window and a needle shield cap engaged with the needle shield. The needle shield cap is used to stop the hub when the hub is moved by the driving unit in a proximal direction from the first to the second position.

It is preferred that the holding unit is formed with a port, the driving unit includes a slider having a second fin, and the second fin passes through the port to lock the slider to the holding unit after the hub is stopped by the activation unit.

It is preferred that the holding unit includes a support formed with a second aperture and a holder formed with the port and a claw which is engaged with the second aperture.

It is preferred that the injection unit further includes a plunger rod, the driving unit includes a slider and a rotator, the plunger rod is received in the slider and movably held by the rotator, and the rotator is rotated by holding unit to release the plunger rod.

It is preferred that the holding unit includes a housing formed with a rail, the rotator is formed with a convexity, and the rotator is rotated due to the convexity being guided by the rail while the slider is moved in a proximal direction.

It is preferred that the rotator is formed with a leg, the plunger rod is formed with an L-shaped slot having a transverse section and a longitudinal section, and the plunger rod is released when the leg is moved along the transverse section to a position aligned with the longitudinal section.

It is preferred that the activation unit includes a first biasing member, a needle shield formed with a first arm and an activator formed with a costa, the holding unit includes a holder formed with a bump, the first biasing member abuts against the needle shield and the holder, and the first arm is confined by the bump and the costa to maintain a state that the needle shield protrudes out of the holding unit in a proximal direction.

It is preferred that the needle shield is further formed with a second arm, the activator is further formed with an ear, the holding unit includes a housing formed with a second finger, the activator is pushed by the second arm in a distal direction such that the ear is engaged with the second finger when the needle shield is pushed back in the distal direction.

It is preferred that the holding unit includes a support formed with a prong and a first aperture, the housing is formed with a first finger, the slider is formed with a first fin, the prong is engaged with the first finger, and the first fin is releasably engaged with the first aperture.

It is preferred that the activator is formed with a lobe, the first fin of the slider is formed with a web, the driving unit further includes a second biasing member which abuts against the slider and the holding unit, and the first fin is released from the first aperture to allow the slider sliding in the proximal direction by the lobe sliding over the web while the activator is pushed in the distal direction.

It is preferred that the needle shield is formed with a third arm, the holding unit is formed with a shoulder, and after the activator is pushed in a distal direction, the first arm slides over the bump to allow the needle shield sliding in the proximal direction till the third arm contacts the shoulder.

It is preferred that the needle shield is formed with a fourth arm, the holding unit is formed with an opening, and the fourth arm is engaged with the opening to prevent the needle shield from being moved in the distal direction when the third arm contacts the shoulder.

Another aspect of this invention is directed to an assembly of an electronic device with a medicament delivery device. The assembly comprises: a casing formed with a first surface and a second surface opposite to the first surface; the electronic device is mounted to the first surface; and the medicament delivery device, is mounted to the second surface.

It is preferred that the casing includes a frame, a casing cap detachably mounted to the frame, and a first communication unit mounted to the frame and electrically connected to the electronic device. The first communication unit sends a signal to start up the electronic device or an app in the electronic device or a function of the electronic device when the casing cap is removed from the frame.

It is preferred that the casing includes two conductive pins fixed to the frame and electrically connected to the first communication unit, and a conductive slip fixed to the casing cap. The conductive slip contacts the conductive pins when the casing cap is mounted to the frame, and wherein the conductive slip is removed from the conductive pins when the casing cap is removed from the frame.

It is preferred that the casing further includes a second communication unit electrically connected to the first communication unit and the conductive pins. The second communication unit detects removal of the conductive slip and sends the signal to the electronic device via the first communication unit. It is preferred that the holding unit is formed with a projection and that the frame is formed with a receptacle for releasably engaging the projection.

BRIEF DESCRIPTION OF THE DRAWINGS

The accompanying drawings illustrate embodiments of the invention and together with the description serve to explain the principles of the invention. In the drawings.

DETAILED DESCRIPTION OF THE INVENTION

In the present invention, the term "proximal part/end" refers to the part/end of the medicament delivery device, or the parts/ends of the members thereof, which is/are located closest to the medicament delivery site of a patient. Correspondingly, the term "distal part/end" refers to the part/end of the medicament delivery device, or the parts/ends of the members thereof, which is/are located farthest away from the medicament delivery site of the patient.

Figure 1:
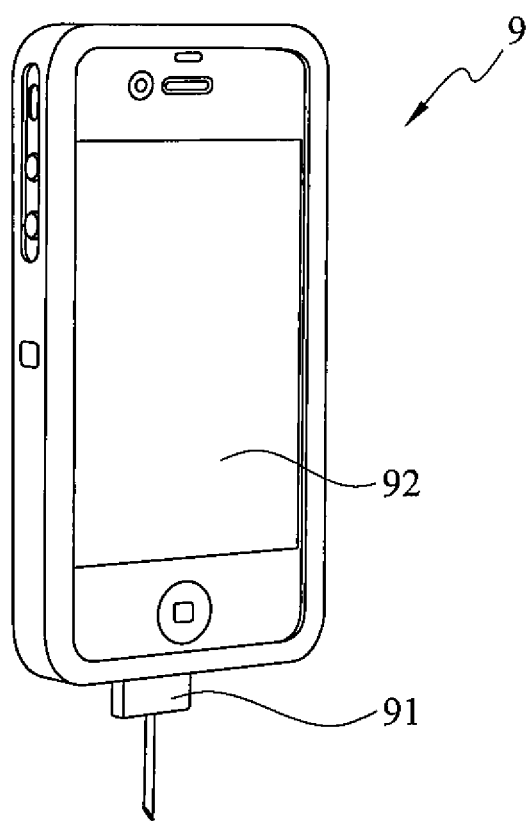
FIG. 1 is an assembled perspective view illustrating a conventional assembly of an auto-injector and a cell phone.
Figure 2:
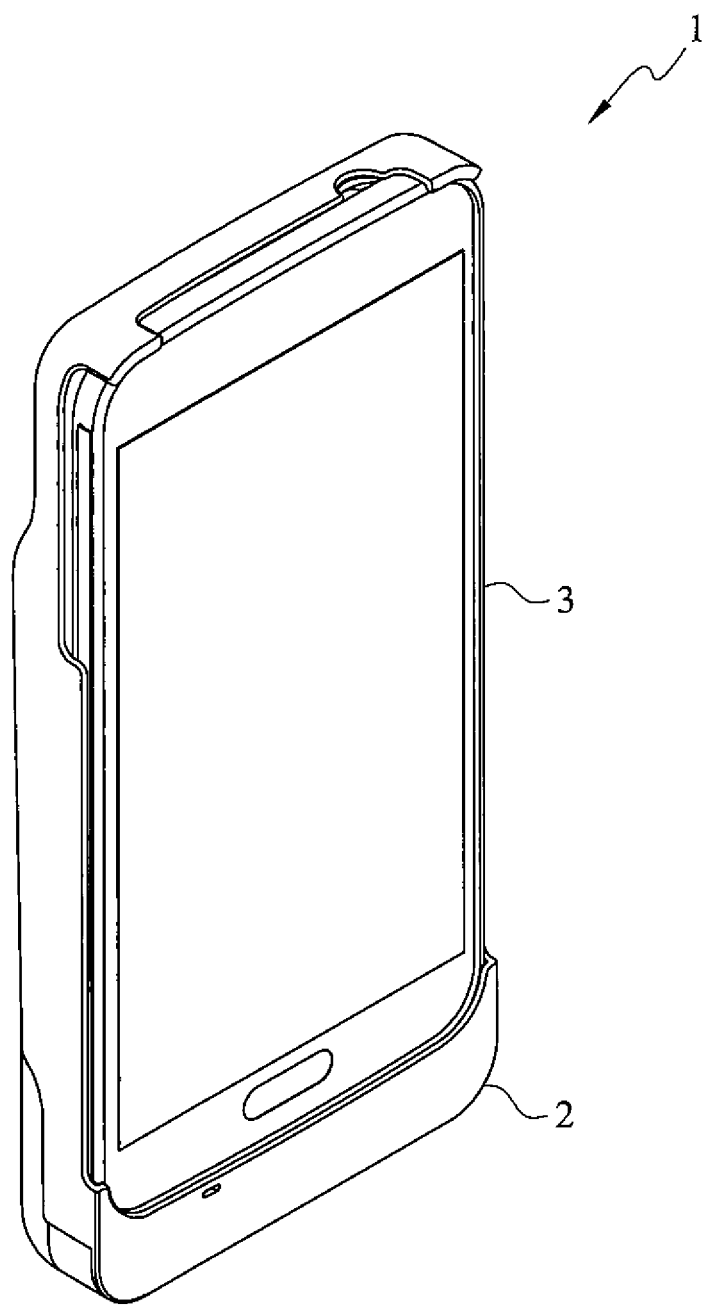
FIG. 2 is an assembled perspective view illustrating an assembly of an electronic device and a medicament delivery device according to this invention.
Figure 3:
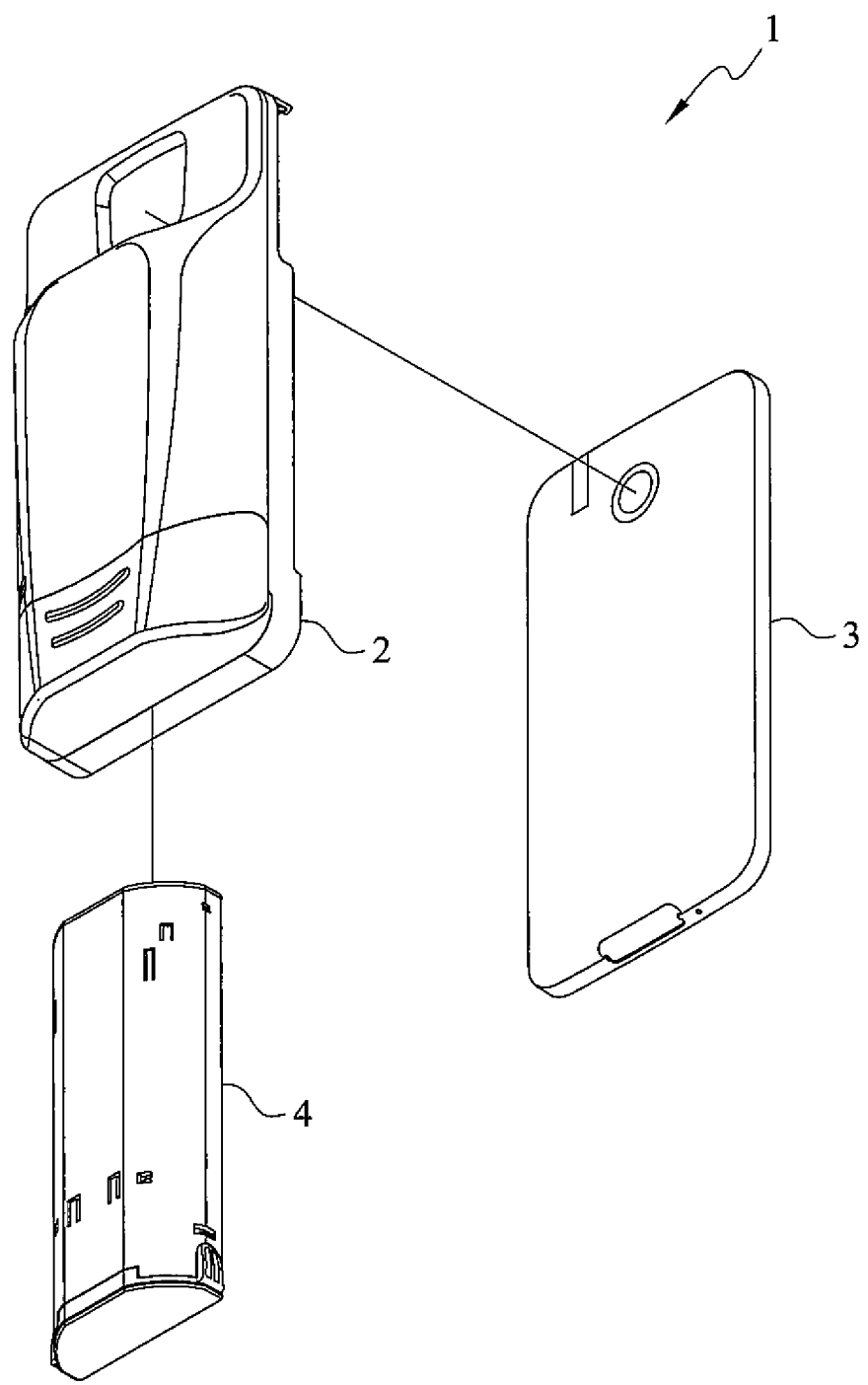
FIG. 3 is an exploded perspective view of the assembly according to this invention.

As shown in FIGS. 2 and 3, an assembly 1 of an electronic device and a medicament delivery device may comprise a casing 2, an electronic device 3 detachably mounted to an outer surface of the casing 2, and the medicament delivery device 4 detachably arranged in the casing 2. In the present invention, the electronic device 3 is, for example, a cell phone.

Figure 4:
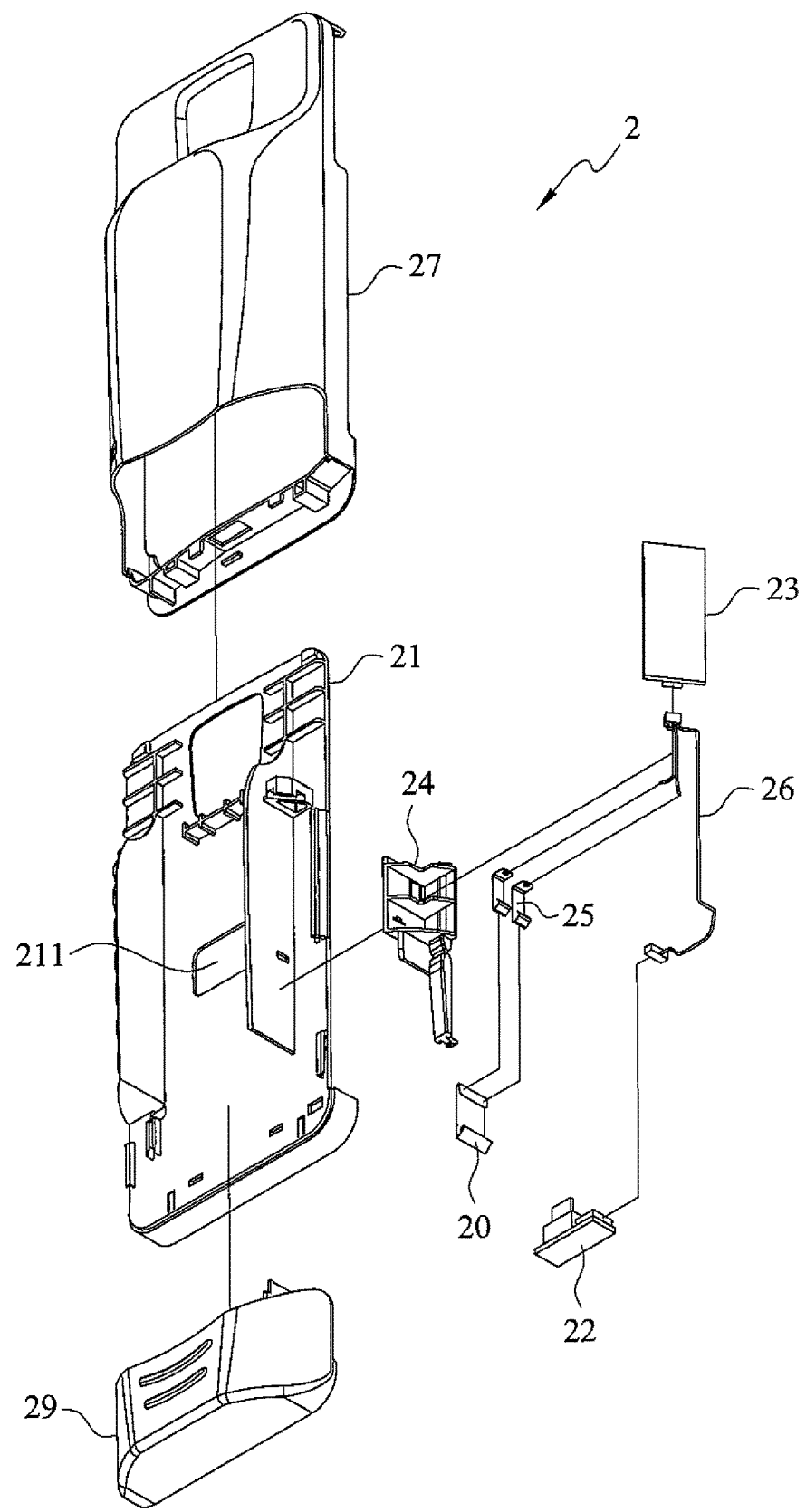
FIG. 4 is an exploded perspective view of the casing of the assembly according to this invention.
Figure 5:
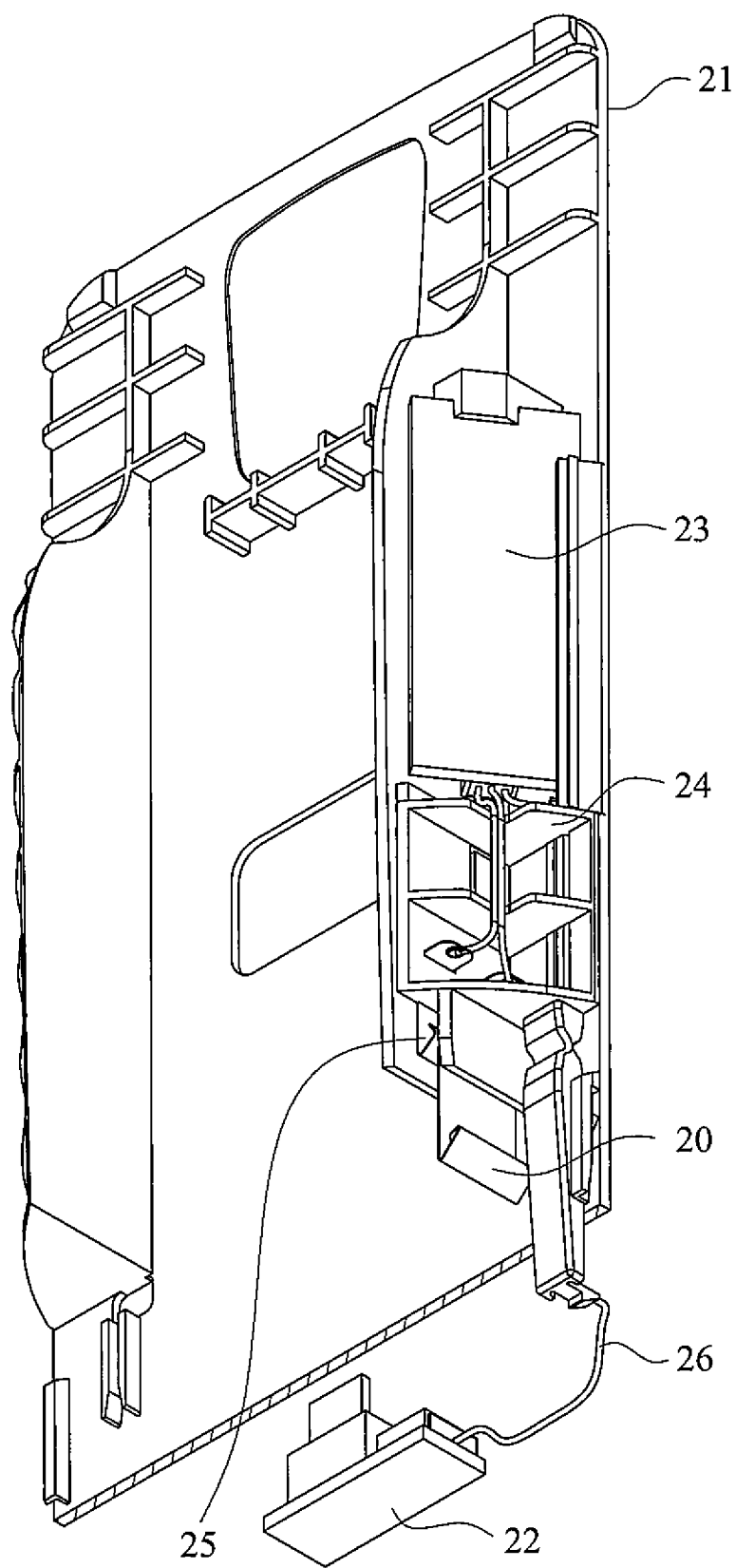
FIG. 5 is an assembled perspective view of the casing of the assembly according to this invention.

As shown in FIGS. 4 and 5, the casing 2 may include a frame 21 formed with a receptacle 211 at a middle section, a first communication unit 22 with a mini USB (Universal Serial Bus) mounted at a proximal end of the frame 21, a second communication unit 23 mounted at the side surface of the frame 21, a bracket 24 mounted at the side surface of the frame 21 and between the first communication unit 22 and the second communication unit 23, two conductive pins 25 mounted to the bracket 24, wiring 26 electrically connecting the second communication unit 23 to the conductive pins 25 and to the first communication unit 22, a cover 27 masking most of the frame 21, a casing cap 29 releasably mounted at proximal end of the frame 21 or cover 27, and a conductive slip 20 mounted to the casing cap 29.

The first communication unit 22 (such as via the mini USB) is electrically connected to the electronic device 3. When the casing cap 29 is mounted to the frame 21 and/or cover 27, the conductive slip 20 contacts the two conductive pins 25. In the attached state, the second communication unit 23 detects that the casing cap 29 is not removed and the medicament delivery device 4 is not used yet. On the contrary, when the casing cap 29 is removed from the frame 21 or cover 27, the conductive slip 20, which is fixed to the casing cap 29, is also removed from the conductive pins 25. In the detached state, the two conductive pins 25 are not electrically connected to each other. The second communication unit 23 detects that the casing cap 29 is removed and the medicament delivery device 4 may be used. Hence, the second communication unit 23 may send a signal to the electronic device 3 through the wiring 26 and the first communication unit 22 so as to automatically activate the electronic device 3.

The activated electronic device 3 may, for example, take pictures of the surroundings or of the user via a camera of the electronic device 3 and/or announce instructions to the user or to transmit an alarm to by-passers via a speaker of the electronic device 3. Alternatively, the activated electronic device 3 may wirelessly communicate data to another cell phone or to a computer via a network. The data may include the GPS location of the electronic device 3, information about the need of emergency services, etc.

Figure 6:
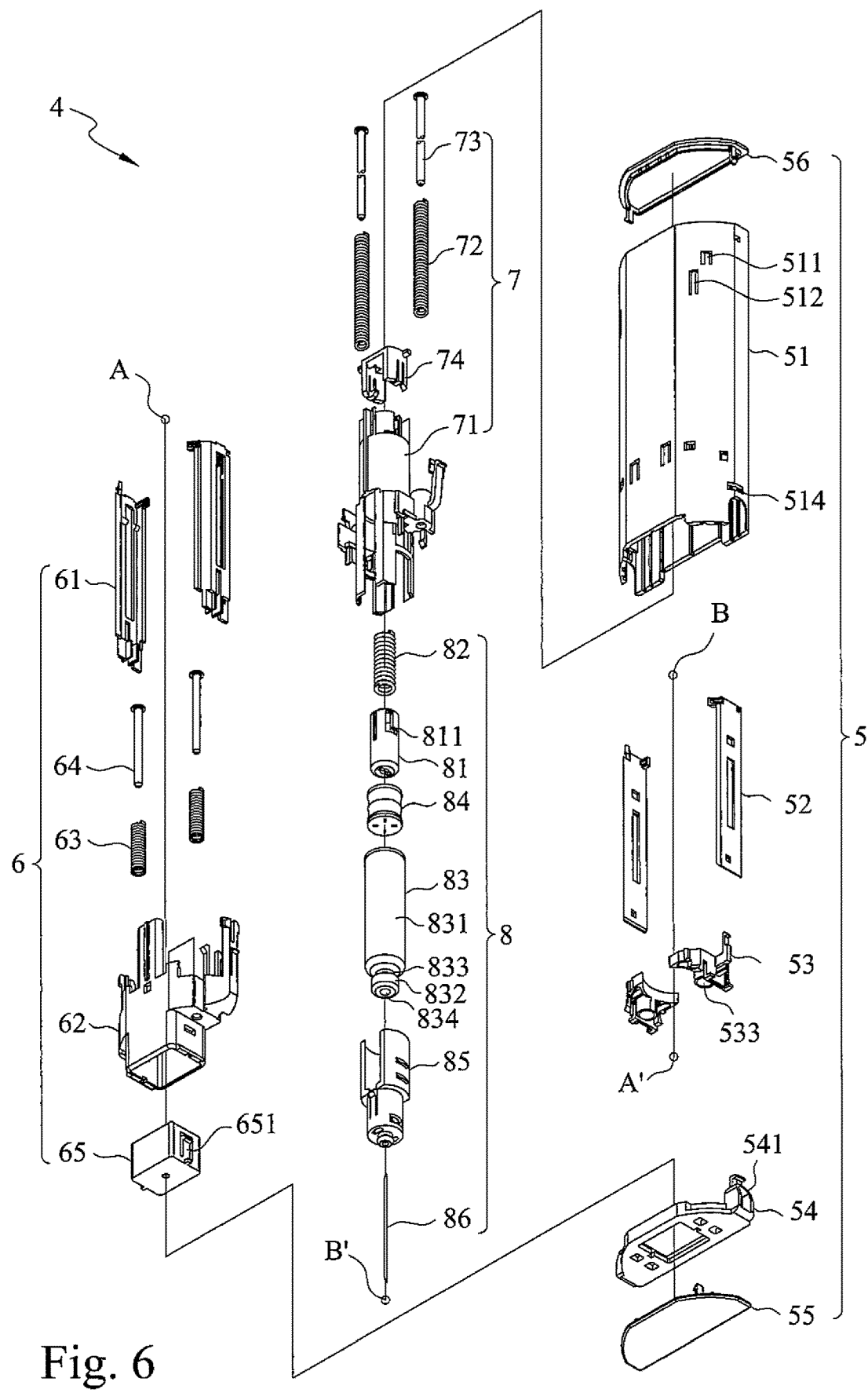
FIG. 6 is an exploded perspective view of the medicament delivery device of the assembly according to this invention.

As shown in FIGS. 3 and 6, the medicament delivery device 4 may comprise a holding unit 5, an activation unit 6 slidable relative to the holding unit, a driving unit 7 releasably engaged to the holding unit 5 and able to be released by the activation unit 6, and an injection unit 8 partially received in the driving unit 7 and able to perform a medicament injection by the aid of the driving unit 7.

The holding unit 5 may include a hollow housing 51, two supports 52 fixedly mounted to the housing 51 at a distal section of the housing 51, two holders 53 fixedly mounted to the housing 51 at a proximal section of the housing 51, an injector cap 54 detachably engaged to a proximal end of the housing 51, a safety cap 55 engaged to the injector cap 54, and a lid 56 detachably engaged to a distal end of the housing 51.

Figure 7:
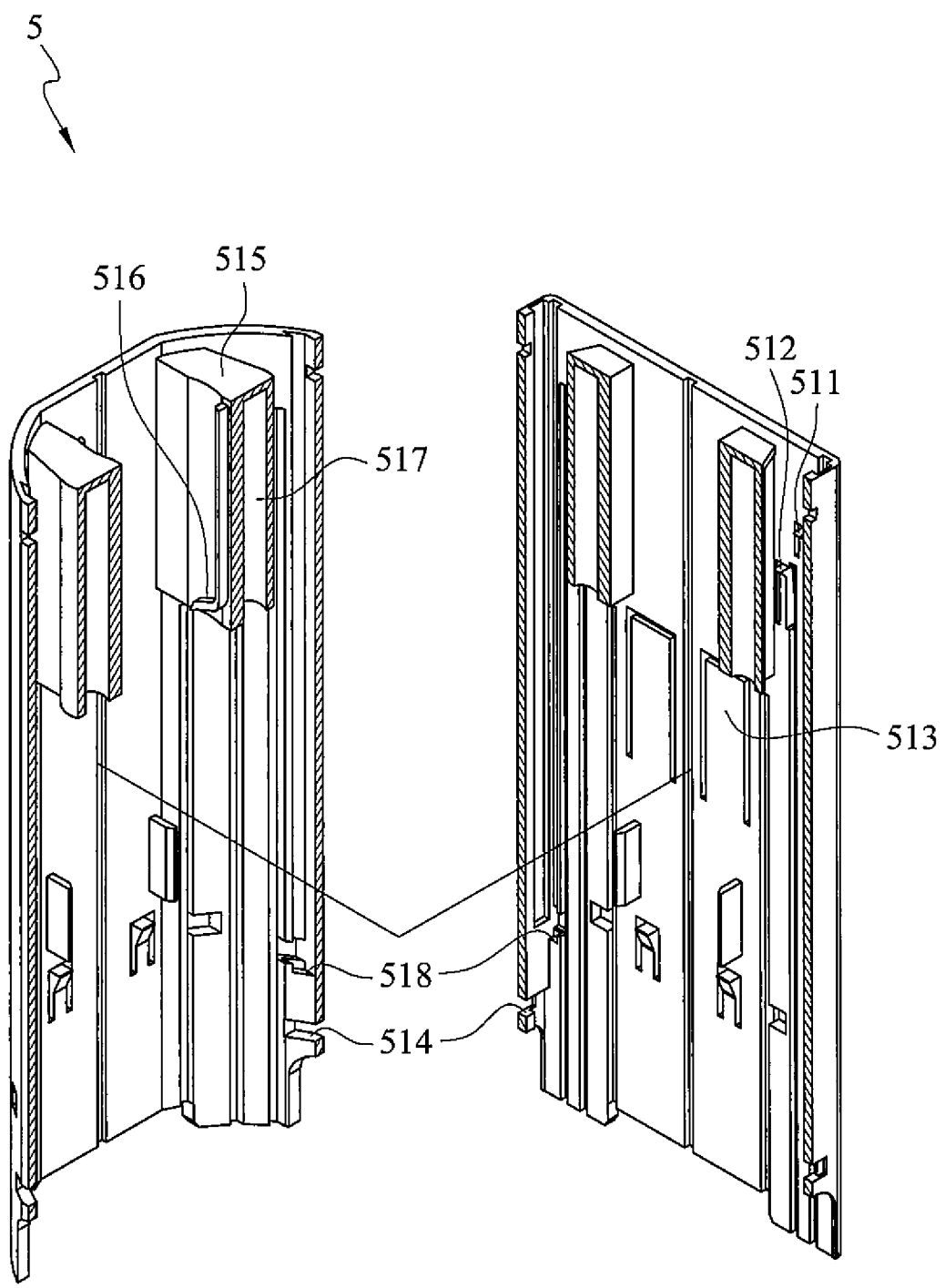
FIG. 7 is a perspective and sectional view of the housing of the medicament delivery device according to this invention.

As shown in FIGS. 6 and 7, the housing 51 may be formed with two first fingers 511 with barbs respectively on two opposite walls of the housing 51 at a distal section, two second fingers 512 with barbs respectively on the two opposite walls at the distal section, two projections 513 at a middle section, two shoulder 518 at a proximal section, two openings 514 at the proximal section, two bridges 515 at the distal section connecting the two opposite walls of the housing 51, two L-shaped rails 516 respectively on the outer surface of the two bridges 515, and two tubes 517 inside the two bridges 515.

Figure 8:
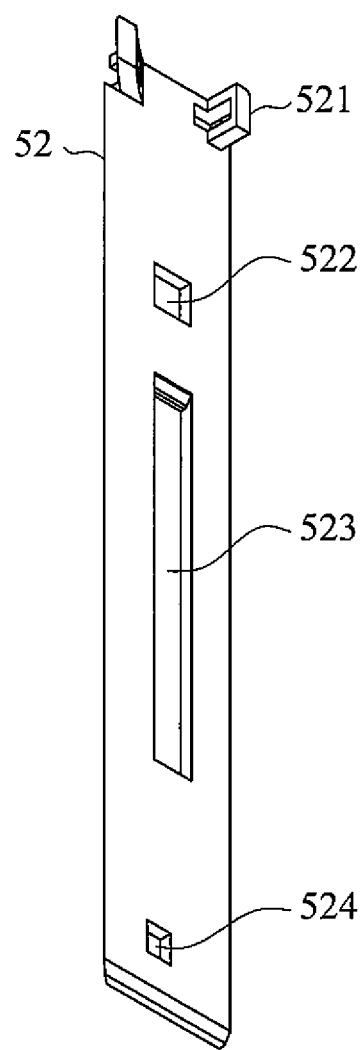
FIG. 8 is a perspective view of the support of the medicament delivery device according to this invention.
Figure 9:
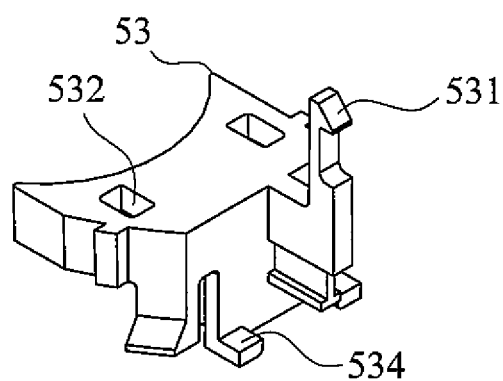
FIG. 9 is a perspective view of the holder of the medicament delivery device according to this invention.

As shown in FIGS. 6 and 8, the support 52 may be formed with two prongs 521 with barbs at a distal end thereof, a first aperture 522 at a middle section, a longitudinal groove 523 at the middle section, and a second aperture 524 at a proximal section. As shown in FIGS. 6 and 9, the holder 53 may be formed with a claw 531 with a barb at a distal end, two ports 532 at a middle section, a bush 533 facing a proximal direction and between the two ports 532, and two bumps 534 at a proximal end.

As shown in FIG. 6, the injector cap 54 may be formed with two wings 541, having barbs, at two sides.

As shown in FIG. 6, the activation unit 6 may include two activators 61 slidably connected to the supports 52, a needle shield 62 slidably received in the housing 51, two first biasing members 63 received in the needle shield 62, two first guide rods 64 received in the first biasing members 63, and a needle shield cap 65 mounted in the needle shield 62.

Figure 10:
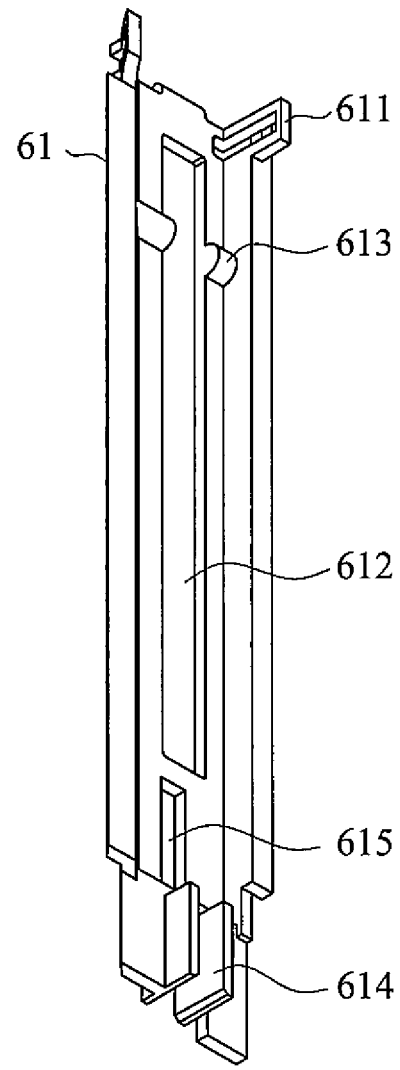
FIG. 10 is a perspective view of the activator of the medicament delivery device according to this invention.

As shown in FIGS. 6 and 10, the activator 61 may be formed with two ears 611, having holes, at a distal end, a longitudinal first flute 612 at a distal section, two lobes 613 at the distal section and respectively at two sides of the first flute 612, a longitudinal second flute 615 at a proximal section, two costae 614 at a proximal end and respectively at two sides of the second flute 615.

Figure 11:
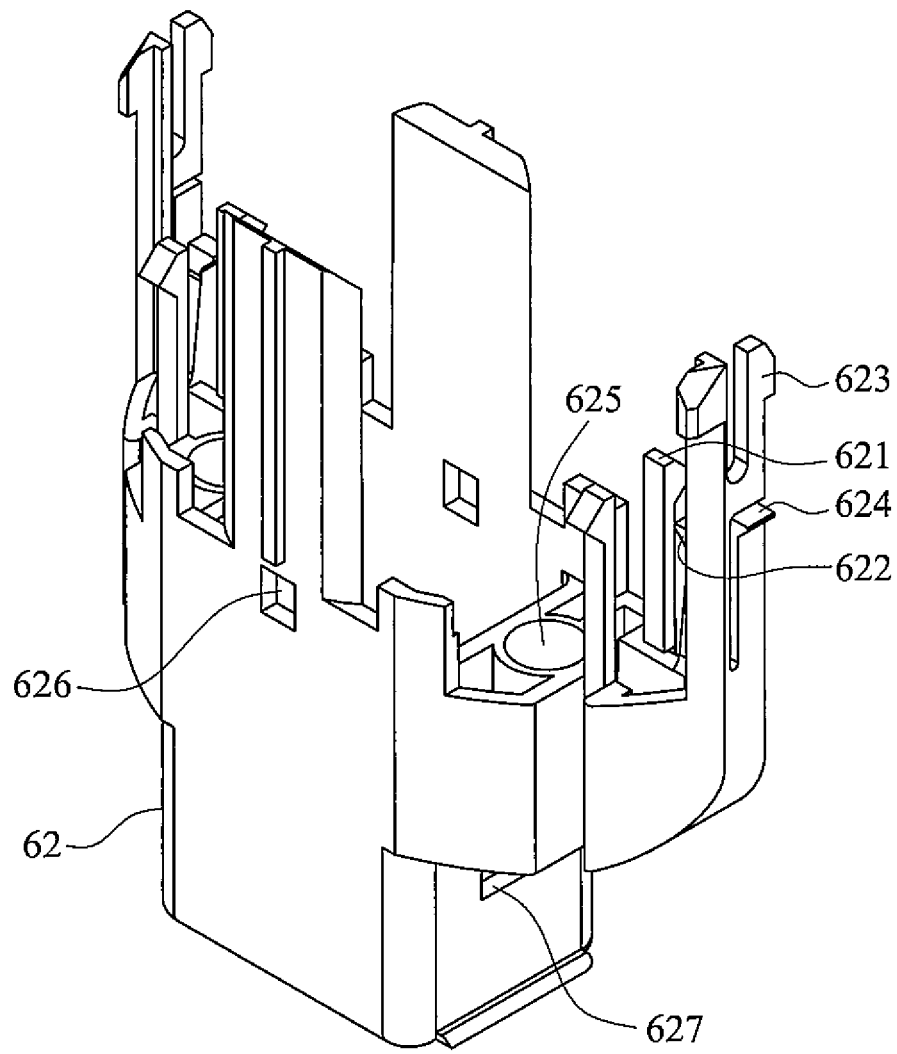
FIG. 11 is a perspective view of the needle shield of the medicament delivery device according to this invention.

As shown in FIGS. 6 and 11, the needle shield 62 may be formed with four first arms 621, two second arms 622, four third arms 623, and two fourth arms 624 all of which extend in a distal direction and have barbs at free ends, two sleeves 625 facing the distal direction, two first windows 626 facing a direction perpendicular to the longitudinal central axis and situated at a middle section, and two second windows 627 facing a direction perpendicular to the longitudinal central axis and a line connecting the two first windows 626 and situated at a proximal section.

As shown in FIG. 6, the needle shield cap 65 may be formed with two detents 651, having barbs, at two sides.

As shown in FIG. 6, the driving unit 7 may include a slider 71 releasably engaged to the supports 52, two second biasing members 72 received in the slider 71, two second guide rod 73 received in the two second biasing members 72, and a rotator 74 rotatably mounted to the slider 71.

Figure 12:
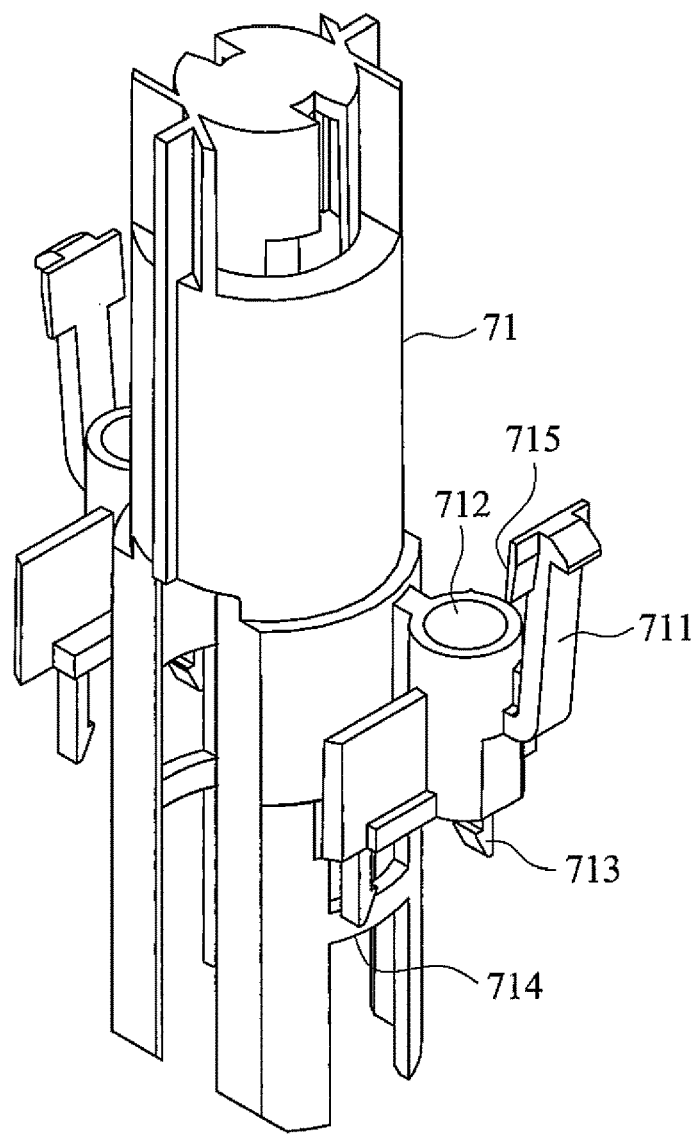
FIG. 12 is a perspective view of the slider of the medicament delivery device according to this invention.

As shown in FIGS. 6 and 12, the slider 71 may be formed with two first fins 711 extending in a distal direction, two collars 712 facing the distal direction, four second fins 713 extending in a proximal direction and with barbs, two transverse ribs 714 at proximal section. Each first fin 711 has, at its free end, a web 715 facing the central axis and a barb facing away the central axis.

Figure 13:
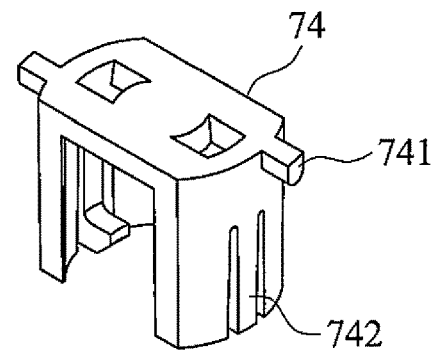
FIG. 13 is a perspective view of the rotator of the medicament delivery device according to this invention.

As shown in FIGS. 6 and 13, the rotator 74 may be formed with two convexities 741 extending in a transverse direction, and two legs 742 (having barbs) extending in a proximal direction.

As shown in FIG. 6, the injection unit 8 may include a plunger rod 81 slidably receiving in the slider 71, a third biasing member 82 receiving in the plunger rod 81, a container 83 received in the slider 71, a stopper 84 slidably received in the container 83, a hub 85 engaged to the slider 71, and a cannula 86 fixed to the hub 85. The plunger rod 81 may be formed with an L-shaped slot 811 which is constituted by a short-transverse section and a long-longitudinal section. The container 83 may be formed with a body 831, a head 832, a neck 833 connecting the head 832 to the body 831 and having an outer diameter smaller than those of the head 832 and body 831, a septum 834 on the head 832 sealing medicament in the container 83.

Figure 14:
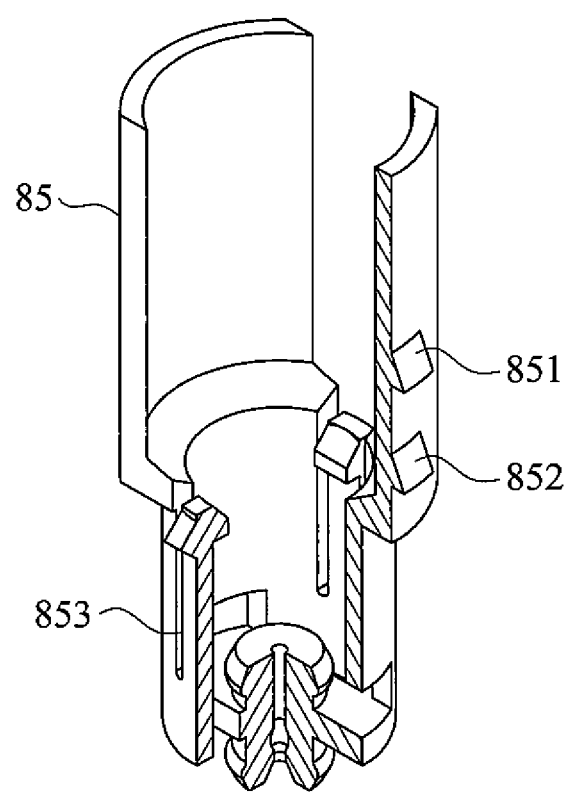
FIG. 14 is a perspective view of the hub of the medicament delivery device according to this invention.

As shown in FIGS. 6 and 14, the hub 85 may be formed with two first wedges 851 and two second wedges 852 at a distal section, and two tongues 853 at a proximal section. Each tongue 853 has, at its free end, an outer barb and an inner barb. The structure of some elements of the medicament delivery device 4 may be symmetric relative to a plane in which the central axis travels. Correspondingly, the medicament delivery device 4 may include two identical elements to be fit with the symmetrical structure. Only one of the two identical elements and one side of the symmetric structure will be mentioned in following assembly process and operation.

First, as shown in FIG. 6, the support 52 is inserted into the housing 51 such that the prong 521 of the support 52 is engaged with and fixed to the first finger 511 of the housing 51. Next, the second guide rod 73 and the second biasing member 72 are put into the collar 712 of the slider 71. The slider 71 together with the second guide rod 73 and the second biasing member 72 is then inserted into the housing 51 such that the second guide rod 73 and the second biasing member 72 are received in the tube 517 of the housing 51 and the barb of the first fin 711 of the slider 71 is engaged in the first aperture 522 of the support 52 to releasably hold the slider 71 to the support 52 even though two ends of the second biasing member 72 respectively abut against the slider 71 and a closed end of the tube 517 of the housing 51.

Subsequently, the activator 61 is inserted into the housing 51 and makes the first fin 711 of the slider 71 be received in the first flute 612 of the activator 61 at a distal end of the first flute 612 such that the first fin 711 prohibits the activator 61 from sliding in the proximal direction but allow the activator 61 sliding in the distal direction. The barb of the first fin 711 passes through the first flute 612 of the activator 61 now and is engaged in the first aperture 522 of the support 52 again. The first flute 612 of the activator 61 may be substantially aligned with the groove 523 of the support 52. Moreover, the holder 53 is inserted into the housing 51 such that the claw 531 of the holder 53 is received in the second flute 615 of the activator 61 and the barb of the claw 531 is engaged in the second aperture 524 of the support 52 so as to fix the holder 53 to the support 52. Furthermore, the first guide rod 64 and the first biasing member 63 are put into the sleeve 625 of the needle shield 62. The needle shield 62 together with the first guide rod 64 and the first biasing member 63 is inserted into the housing 51. Two ends of the first biasing member 63 respectively abut against the needle shield 62 and a closed end of the bush 533 of the holder 53. After the insertion of the needle shield 62, the injector cap 54 is immediately mounted to the housing 51 by the barb of the wing 541 of the injector cap 54 being snapped into the opening 514 of the housing 51 so as to confine the needle shield 62 in the housing 51.

After that, the third biasing member 82 and the plunger rod 81 are put into the slider 71 from the proximal end and the rotator 74 is mounted at the distal end of the slider 71 such that the barb of the leg 742 of the rotator 74 passes through the slider 71 and is received in the short-transverse section of the slot 811 of the plunger rod 81 and that two ends of the third biasing member 82 respectively abut against a proximal end of the plunger rod 81 and a distal end of the slider 71. Furthermore, the container 83 is inserted into the slider 71 at the distal end. Moreover, the cannula 86 is fixed to the hub 85. The hub 85 together with the cannula 86 is put into the slider 71 such that the first wedge 851 of the hub 85 is engaged with the rib 714 of the slider 71 so as to hold the hub 85 to the slider 71 and thus confine the container 83 inside the slider 71 via the hub 85. The proximal end of the cannula 86 does not protrude out of the proximal end of the housing 51 now. Besides, the distal end of the cannula 86 is outside the septum of the container 83 now. In other words, the cannula 86 does not fluidly communicate with the container 83 at present time. Specifically, the septum 834 of the container 83 is not yet pierced by the cannula 86 for the time being.

Then, the needle shield cap 65 is inserted into the needle shield 62 such that the barb of the detent 651 of the needle shield cap 65 is engaged in the second window 627 of the needle shield 62 in order to fix the needle shield cap 65 to the needle shield 62. Next, the safety cap 55 is mounted to the injector cap 54. Finally, the lid 56 is mounted to the housing 51 at the distal end to complete the assembling process of the medicament delivery device 4.

The medicament delivery device 4 may be mounted to the frame 21 by the projection 513 of the housing 51 being engaged in the receptacle 211 of the frame 21. After the cover 27 is mounted to the frame 21, the general assembly 1 is obtained.

Figure 15:
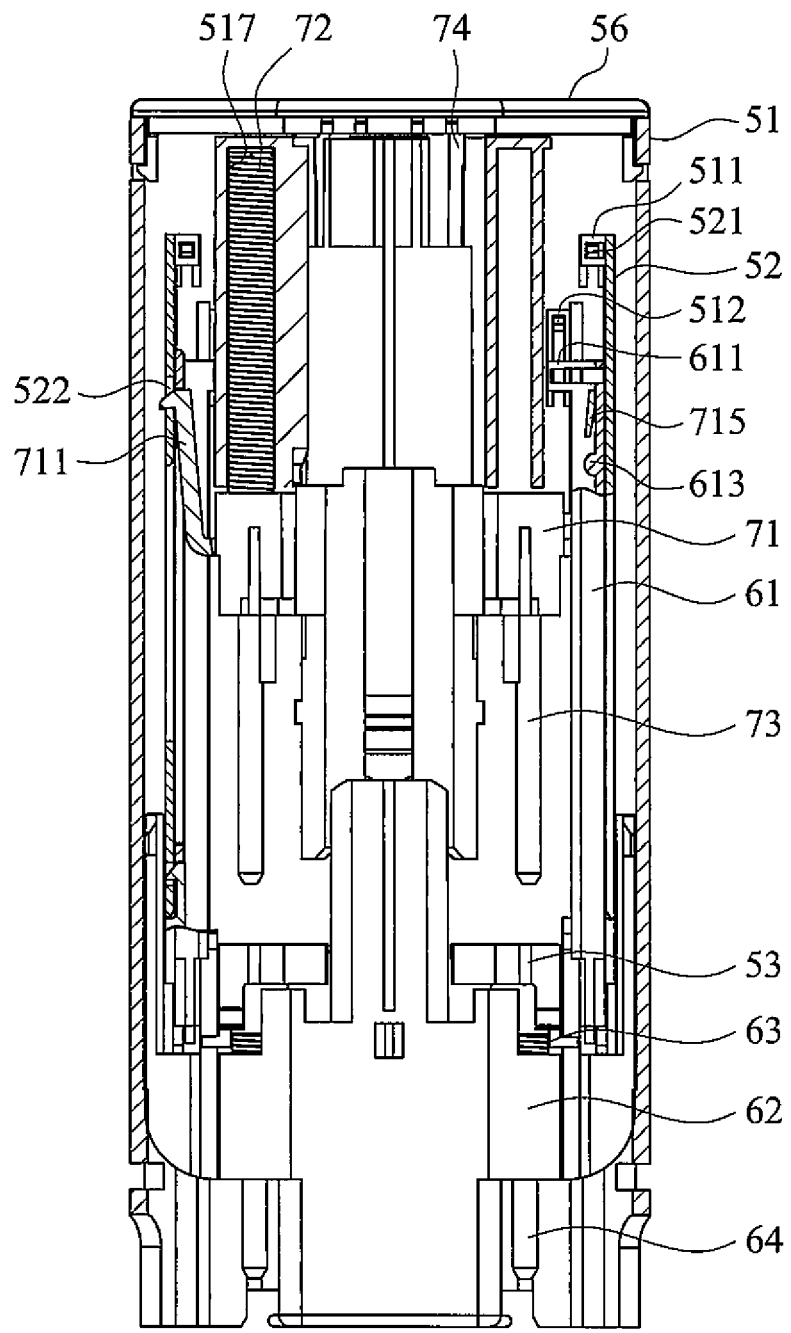
FIG. 15 is an assembled cross-sectional view of the medicament delivery device according to this invention illustrating that the injector cap has been removed and the needle shield has not extended yet.
Figure 16:
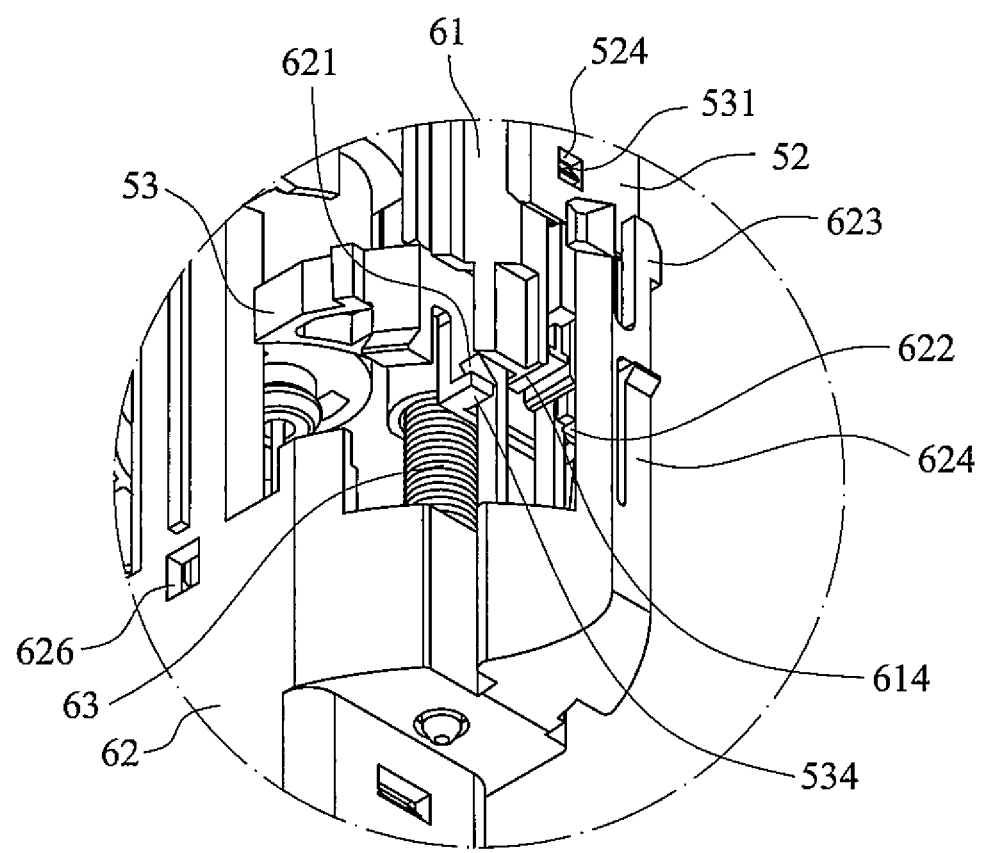
FIG. 16 is a partial perspective view of the of the medicament delivery device according to this invention illustrating that the first arm of the needle shield is confined between the holder and the activator.

When a medicament injection is needed, the casing cap 29 of the general assembly 1 of the electronic device and medicament delivery device should be removed firstly. Next, the wing 541 of the injector cap 54 of the medicament delivery device 4 is pushed inwards (close to a longitudinally central axis of the medicament delivery device 4) to release the barb of the wing 541 from the housing 51 such that the injector cap 54 together with the safety cap 55 may be removed from the housing 51 along the proximal direction, as shown in FIG. 15. Upon the injector cap 54 being removed, the needle shield 62 together with the needle shield cap 65 pops, due to recovery force of the first biasing member 63, out of the proximal end of the housing 51 such that the first arm 621 of the needle shield 62 is hung on the bump 534 of the holder 53. Besides, as shown in FIG. 16, the distal end of the first arm 621 of the needle shield 62 is confined between the holder 53 and the activator 61 so that the first arm 621 of the needle shield 62 cannot bend and surpass the bump 534 of the holder 53 to drop lower. The distal end of the second arm 622 of the needle shield 62 is situated under a proximal end of the activator 61 at present time.

Figure 17:
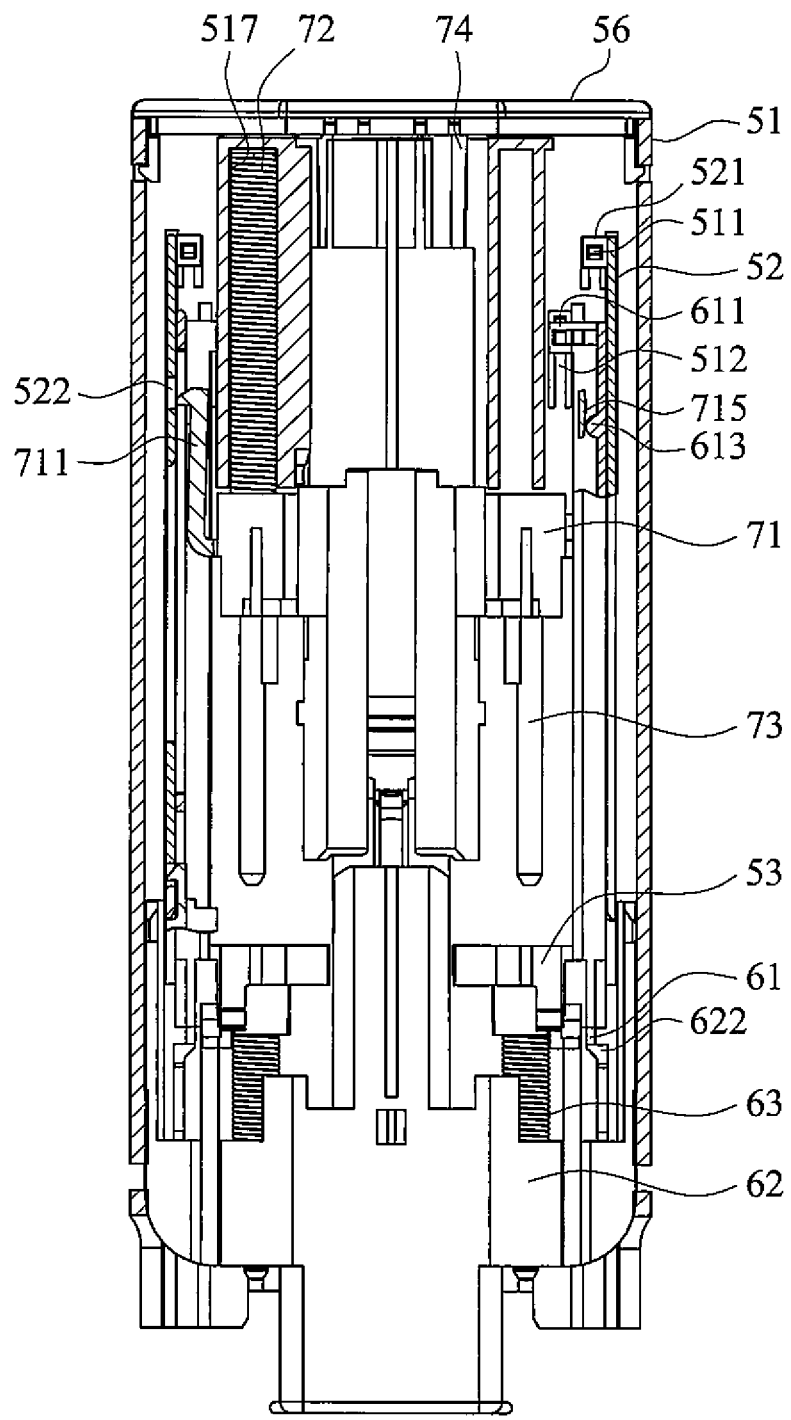
FIG. 17 is an assembled cross-sectional view of the medicament delivery device according to this invention illustrating that the lobe of the activator contacts the web of the slider to release the first fin of the slider from the support.

A user can now hold the general assembly 1 and push the proximal end of the needle shield 62 (or needle shield cap 65) against her/his skin such that the proximal end of the needle shield 62 is almost flush with the proximal end of the housing 51. As shown in FIG. 17, the second arm 622 of the needle shield 62 simultaneously pushes against the proximal end of the activator 61 to slide the activator 61 along the housing 51 in the distal direction till the second finger 512 of the housing 51 snaps into the hole of the ear 611 of the activator 61. During this step and before the ear 611 reaches the first finger 511, the lobe 613 of the activator 61 contacts the web 715 of the slider 71 and bends the first fin 711 of the slider 71 close to the central axis to the extent that the barb of the first fin 711 is released from the first aperture 522 of the support 52.

Since the slider 71 is released from the support 52, the second biasing member 72 pushes down the slider 71 together with the rotator 74, plunger rod 81, third biasing member 82, container 83, hub 85 and cannula 86. Thus, the hub is moved by the drive unit from a first position, in which a proximal end of the cannula is concealed in the activation unit and a distal end of the cannula is outside the container, to a second position, in which the proximal end of the cannula protrudes from the activation unit (6) and the distal end of the cannula is outside the container and wherein the container is also moved with the hub.

Figure 18:
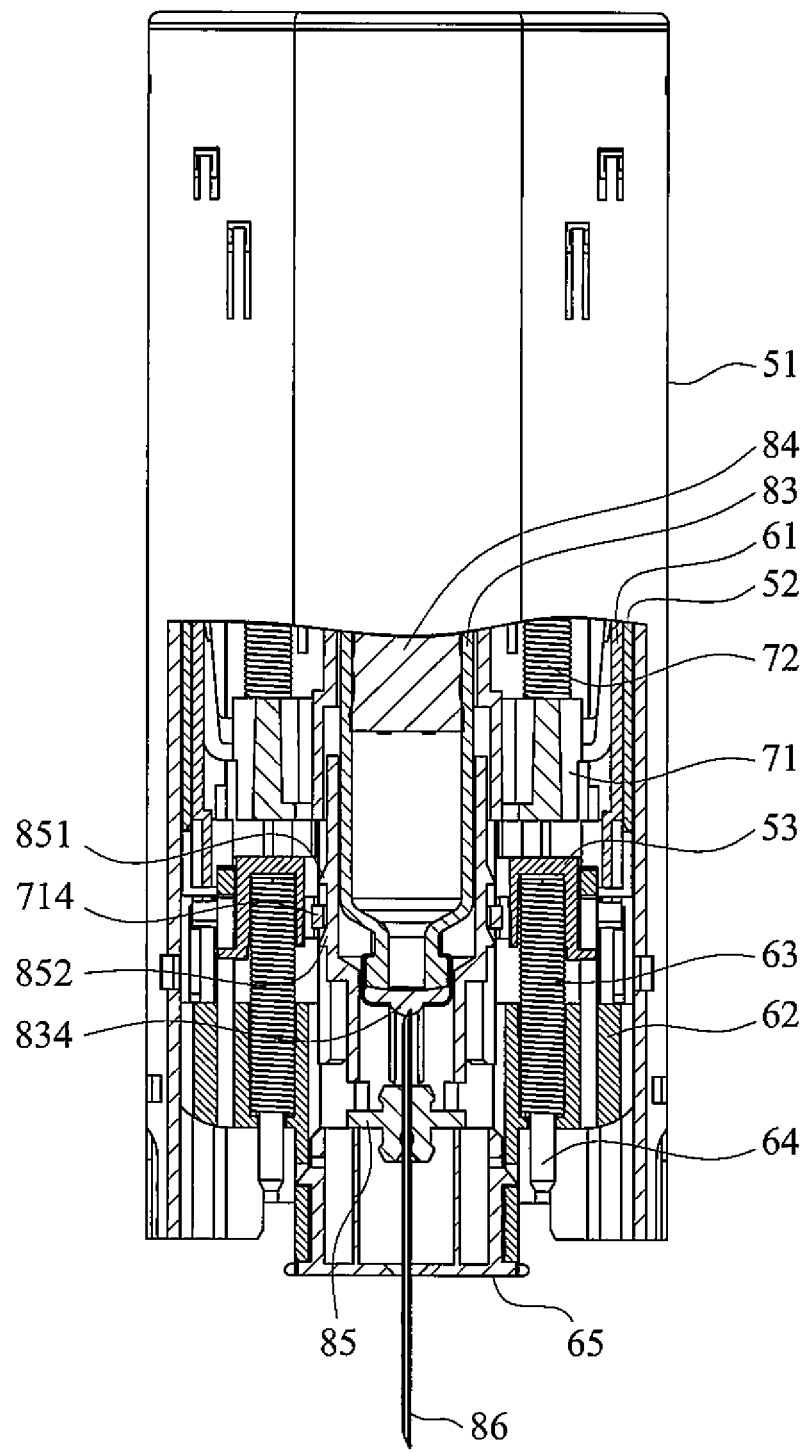
FIG. 18 is a partial cross-sectional view of the medicament delivery device illustrating that the hub proximally slides to contact the needle shield cap and that the septum of the container is not yet penetrated by the cannula.

As shown in FIG. 18, among such a group of moved elements, the hub 85 first contacts the needle shield cap 65 and is stopped. Before the contact occurs, the proximal end of the cannula 86 has protruded out of the needle shield cap 65 and thus penetrated the user's skin. After the contact occurs, the slider 71 continues sliding in the proximal direction due to recovery force of the second biasing member 72 such that four events happen within a short period of time in the following orders: container penetration, slider locking, container locking and medicament injection.

Figure 19:
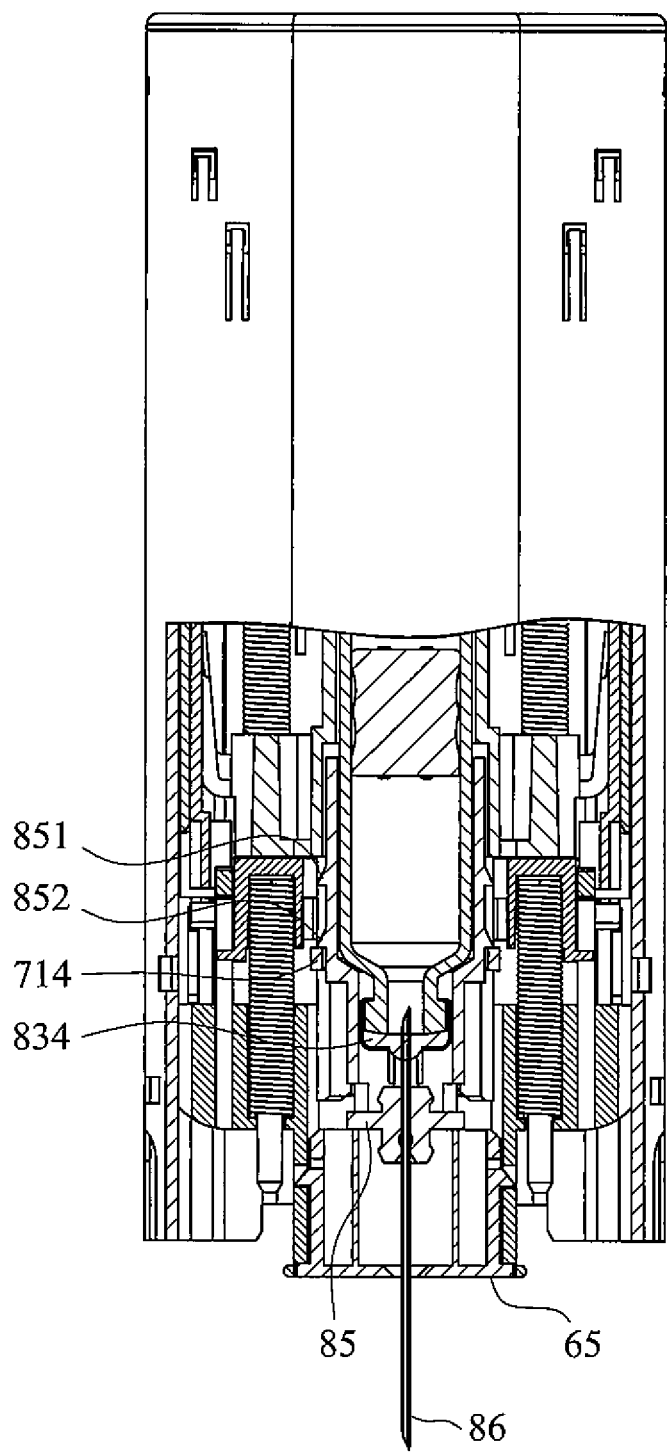
FIG. 19 is a partial cross-sectional view of the medicament delivery device illustrating that the rib of the slider proximally slides over the second wedge of the hub and that the septum of the container is penetrated by the cannula.

Although movement of the hub 85 together with the cannula 86 is stopped by the needle shield cap 65, (the first event shown in FIG. 19) the force of the second biasing member 72 is strong enough to make the rib 714 of the slider 71 proximally slide over the second wedge 852 of the hub 85. In other words, the container 83 together with the slider 71 can continue sliding in the proximal direction till the septum 834 of the container 83 is penetrated by the distal end of the cannula 86. I.e., the container is moved from an initial position, in which the container moves with the hub from the first to the second position, to a final position relative to the hub, in which the container is released from the hub such that the septum is penetrated by the distal end of the cannula.

Figure 20:
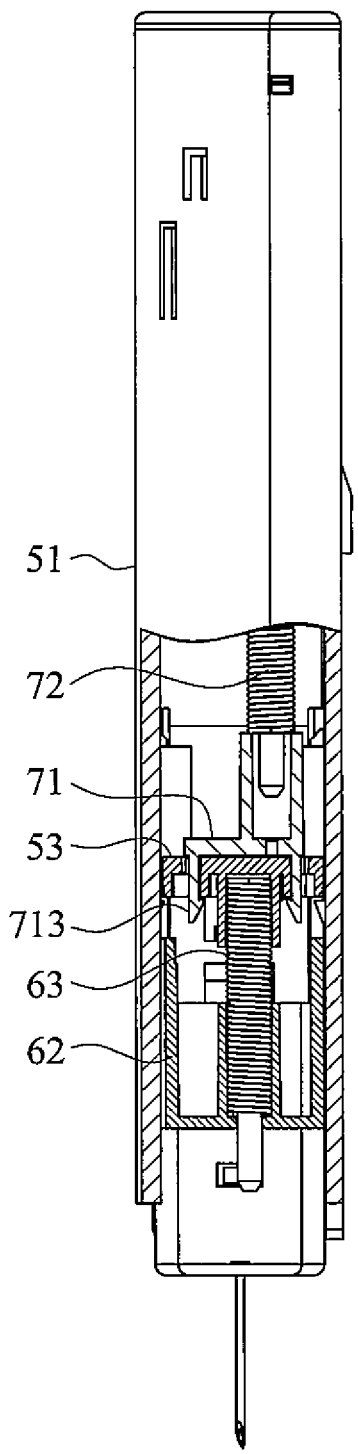
FIG. 20 is a partial cross-sectional view of the medicament delivery device illustrating that the second fin of the slider snaps into the port of the holder and that the slider is locked to the holder.
Figure 21:
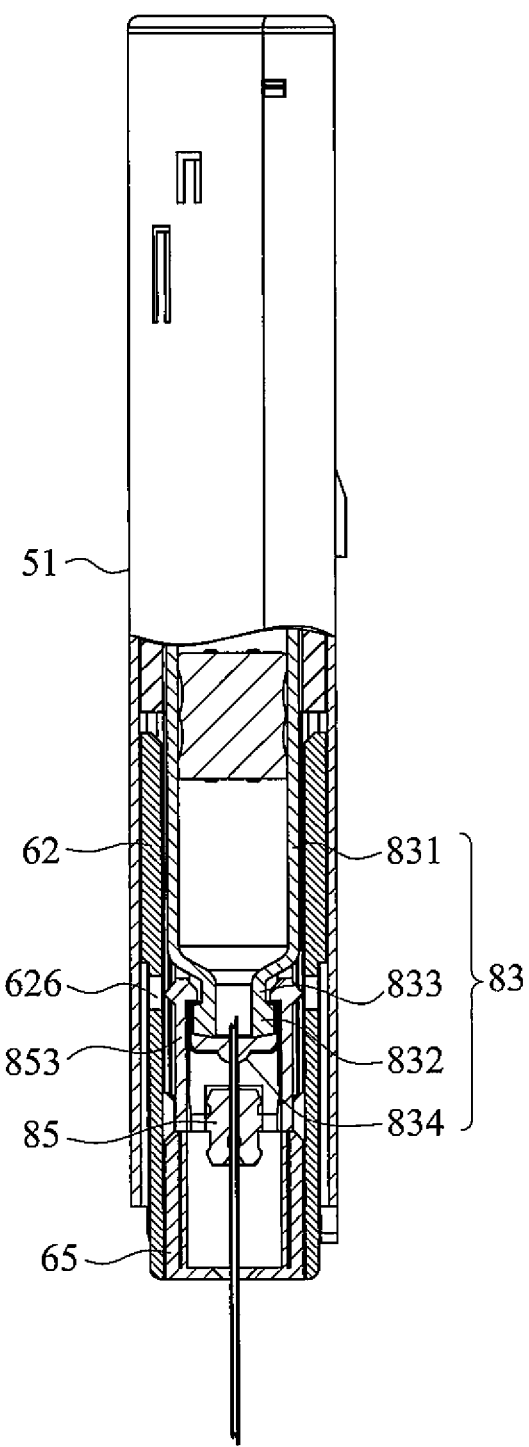
FIG. 21 is a partial cross-sectional view of the medicament delivery device illustrating that the neck of the container is locked by the tongue of the hub.
Figure 22:
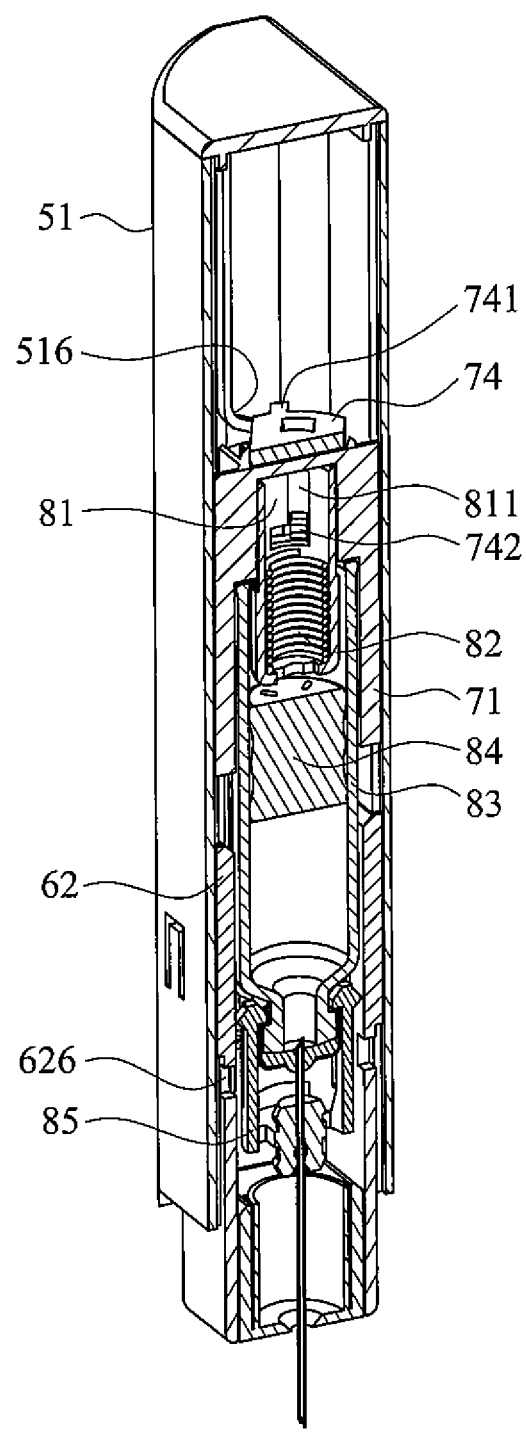
FIG. 22 is a cross-sectional view of the medicament delivery device illustrating that the rotator is rotated by the rail of the housing so as to release the plunger rod.

Next (the second event shown in FIG. 20), the second fin 713 of the slider 71 snaps into the port 532 of the holder 53 and is locked to the holder 53. Furthermore (the third event shown in FIG. 21), because the first window 626 of the needle shield 62 is now aligned with and can receive the outer barb of the tongue 853 of the hub 85, the head 832 of the container 83 can slide over the inner barb of the tongue 853 of the hub 85 and then allows the tongue 853 locking the container 83 at its neck 833. Subsequently (the fourth event shown in FIG. 22), while the rotator 74 together with the slider 71 moves in the proximal direction, the rotator 74 is rotated relative to the slider 71 due to the convexity 741 of the rotator 74 being guided by the L-shaped rail 516 of the housing 51. At opposite end of the rotator 74, the barb of the leg 742 of the rotator 74 is also rotated along the short-transverse section of the L-shaped slot 811 of the plunger rod 81 to align with the long-longitudinal section of the L-shaped slot 811. Because the barb of the leg 742 of the rotator 74 is allowed to slide along the long-longitudinal section of the L-shaped slot 811, the third biasing member 82 now can push the plunger rod 81 in the proximal direction to trigger an injection. Due to abutment of the plunger rod 81 against the stopper 84, the movement of the plunger rod 81 together with the stopper 84 can expel medicament in the container 83 into the user's body through the cannula 86. When the distal end of the long-longitudinal section of the L-shaped slot 811 contacts the barb of the leg 742 of the rotator 74, the movement of the plunger rod 81 is stopped and the injection is completed.

Figure 23:
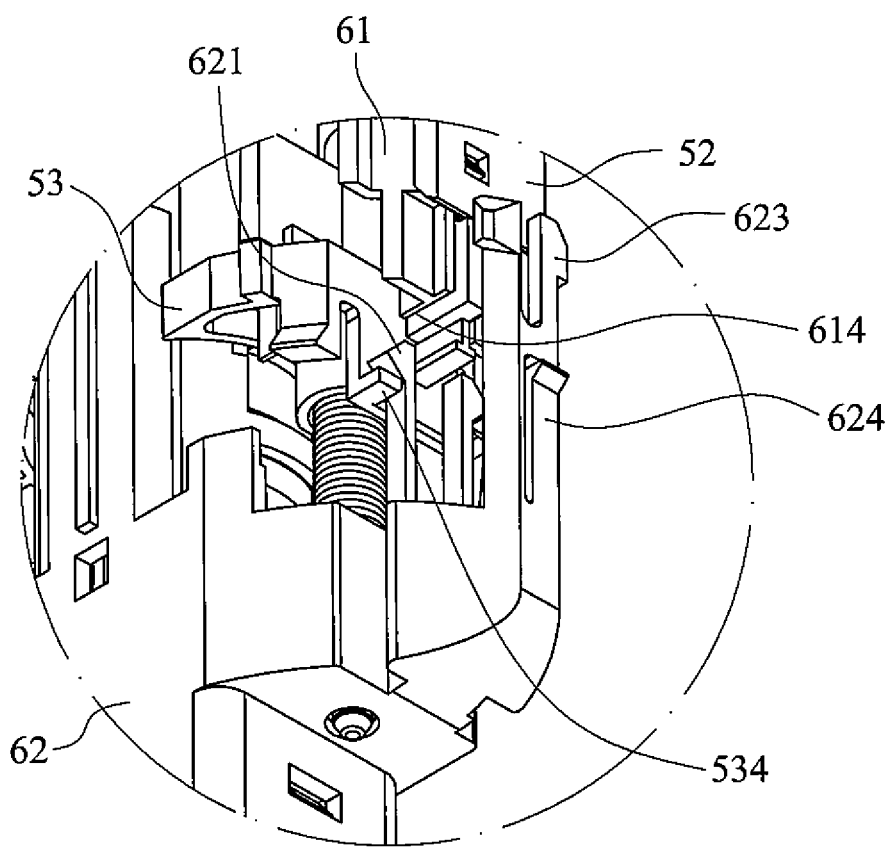
FIG. 23 is a partial perspective view illustrating that the first arm of the needle shield no longer abuts against the activator so that the first arm can slip over the bump of the holder.
Figure 24:
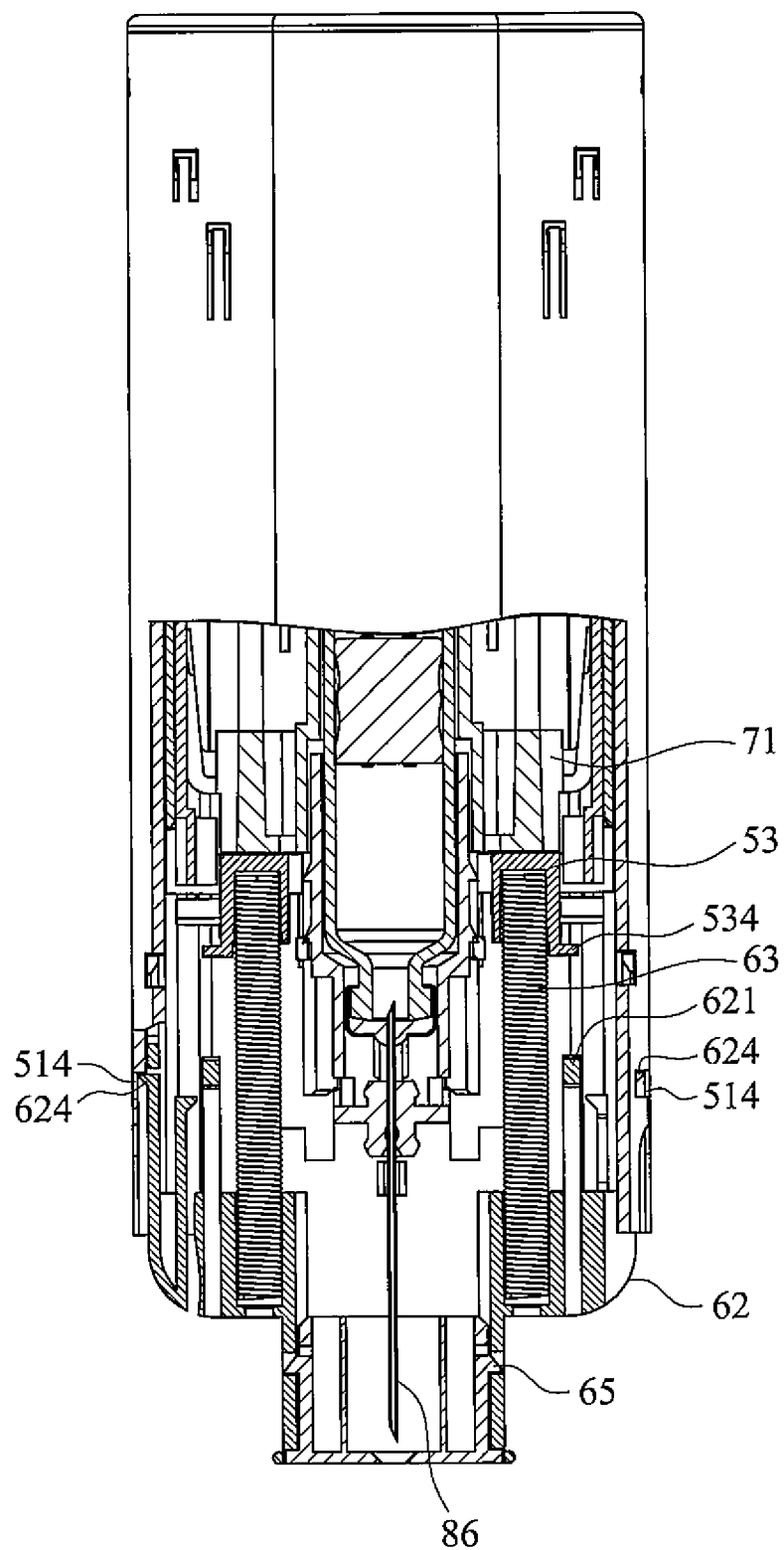
FIG. 24 is a partial cross-sectional view of the medicament delivery device illustrating that the cannula is completely accommodated in the needle shield and that the fourth arm of the needle shield snaps into the opening of the housing.

As shown in FIG. 23, because the activator 61 has been pushed in the distal direction by the second arm 622 of the needle shield 62 and locked by the second finger 512 of the housing 51 in previous step, the first arm 621 of the needle shield 62 no longer abuts against the rib 614 of the activator 61 so that the first arm 621 can be bent now. Hence, as shown in FIG. 24, when the user lifts the medicament delivery device 4 from the skin, the first biasing member 63 can push the needle shield 62 together with the needle shield cap 65 in the proximal direction such that the first arm 621 of the needle shield 62 slips over the bump 534 of the holder 53. Since the first arm 621 of the needle shield 62 is totally released, movement of the needle shield 62 continues in the proximal direction till the third arm 623 of the needle shield 62 contacts the shoulder 518 of the housing 51. On one hand, movement of the needle shield 62 in the proximal direction is stopped by the shoulder 518 of the housing 51 abutting against the barb of the third arm 623 of the needle shield 62. The cannula 86 is completely accommodated in the needle shield 62 now. On the other hand, movement of the needle shield 62 in the distal direction is stopped by the fourth arm 624 of the needle shield 62 snapping into the opening 514 of the housing 51.

Therefore, even if a force is applied to the needle shield 62 in the distal direction (for example, the medicament delivery device 4 is again used to abut the distal end of the needle shield 62 against the skin), the needle shield 62 cannot be moved in the distal direction relative to the housing 51 whereby the needle shield 62 can provide a function of shielding the cannula 86.

After the injection is completed and the general assembly 1 is lifted from the user's skin, the electronic device 3 may be removed from the casing 2 to allow the user's finger pushing the projection 513 of the housing 51 away from the receptacle 211 of the frame 21. The used medicament delivery device 4 then may be removed from the general assembly 1 and be discarded. Subsequently, a new medicament delivery device 4 may be mounted to the casing 2 by the projection 513 of the housing 51 being engaged in the receptacle 211 of the frame 21. When the cover 27, casing cap 29 and electronic device 3 are mounted to the frame 21 finally, the general assembly 1 returns back its initial condition again.

This invention has been disclosed in terms of specific embodiments. It will be apparent that many modifications can be made to the disclosed structures without departing from the invention. Therefore, it is the intent of the appended claims to cover all such variations and modifications that are within the scope of this invention.

The invention claimed is:

1. A medicament delivery device comprising:
a holding unit;
a driving unit releasably connected to the holding unit;
an activation unit slidable relative to the holding unit and arranged to release the driving unit from the holding unit; and
an injection unit configured to be moved by the driving unit;
characterized in that the injection unit includes:
a hub releasably connected to the driving unit (7);
a cannula fixed to the hub; and
a container releasably connected to the hub and wherein the container comprises a septum;
wherein the hub is configured to be moved by the driving unit from a first position, in which a proximal end of the cannula is concealed in the activation unit and a distal end of the cannula is outside the container, to a second position, in which the proximal end of the cannula protrudes from the activation unit and the distal end of the cannula is outside the container and wherein the container is configured to be moved from an initial position, in which the container moves with the hub from the first to the second position, to a final position relative to the hub, in which the container is released from the hub such that the septum is penetrated by the distal end of the cannula,
wherein the driving unit includes a slider and a rotator, the injection unit further includes a plunger rod received in the slider and releasably held by the rotator,
wherein the holding unit includes a housing having a rail, the rotator includes a convexity, and the rotator is rotated due to the convexity being guided by the rail while the slider is moved in a proximal direction.

2. The medicament delivery device according to claim 1, wherein the hub is configured to be stopped by the activation unit when it reaches the second position.

3. The medicament delivery device according to claim 2, wherein the activation unit includes a needle shield and a needle shield cap engaged with the needle shield, and wherein the needle shield cap is arranged to stop the hub when the hub is moved by the driving unit in the proximal direction from the first to the second position.

4. The medicament delivery device according to claim 3, wherein the holding unit prevents the needle shield from being moved distally after the medicament delivery device is lifted from an injection site.

5. The medicament delivery device according to claim 2, wherein the holding unit includes a port, the slider having a fin, and wherein the fin passes through the port to lock the slider to the holding unit when the hub is in the second position.

6. The medicament delivery device according to claim 5, wherein the holding unit includes a support having an aperture and a holder having the port and a claw which is engaged with the aperture.

7. The medicament delivery device according to claim 1, wherein the hub has a tongue, the container has a body, a head and a neck connecting the head to the body, and wherein the tongue is engaged with the neck to lock and stop the container when the container reaches the final position.

8. The medicament delivery device according to claim 7, wherein the activation unit includes a first window which is aligned with the tongue to allow the head sliding over the tongue when the container is moved from the initial position to the final position.

9. The medicament delivery device according to claim 1, wherein the rotator includes a leg, the plunger rod includes a L-shaped slot having a transverse section and a longitudinal section, and the plunger rod is released when the leg is moved along the transverse section to a position aligned with the longitudinal section.

10. An assembly of an electronic device with a medicament delivery device, the assembly comprising:
a casing;
an electronic device electrically communicated to the casing; and
the medicament delivery device according to claim 1, which is mounted to the casing.

11. The assembly of an electronic device with a medicament delivery device according to claim 10, wherein the casing includes a frame, a casing cap detachably mounted to the frame, and a first communication unit mounted to the frame and electrically connected to the electronic device, and wherein the first communication unit is arranged to send a signal to activate the electronic device or an app in the electronic device or a function of the electronic device when the casing cap is removed from the frame.

12. The assembly of an electronic device with a medicament delivery device according to claim 11, wherein the casing includes two conductive pins fixed to the frame and electrically connected to the first communication unit, and a conductive slip fixed to the casing cap, wherein the conductive slip contacts the conductive pins when the casing cap is mounted to the frame, and wherein the conductive slip is arranged to be removed from the conductive pins when the casing cap is removed out of the frame.

13. The assembly of an electronic device with a medicament delivery device according to claim 12, wherein the casing further includes a second communication unit electrically connected to the first communication unit and the conductive pins, and wherein the second communication unit is arranged to detect removal of the conductive slip and to send the signal to the electronic device via the first communication unit.

14. A medicament delivery device comprising:
a holding unit
a driving unit releasably connected to the holding unit
an activation unit slidable relative to the holding unit and arranged to release the driving unit from the holding unit and
an injection unit configured to be moved by the driving unit
characterized in that the injection unit includes:
a hub releasably connected to the driving unit
a cannula fixed to the hub; and
a container releasably connected to the hub and wherein the container comprises a septum;

wherein the hub is configured to be moved by the driving unit from a first position, in which a proximal end of the cannula is concealed in the activation unit and a distal end of the cannula is outside the container, to a second position, in which the proximal end of the cannula protrudes from the activation unit and the distal end of the cannula is outside the container and wherein the container is configured to be moved from an initial position, in which the container moves with the hub from the first to the second position, to a final position relative to the hub, in which the container is released from the hub such that the septum is penetrated by the distal end of the cannula, wherein the hub has a tongue, the container has a body, a head and a neck connecting the head to the body, and wherein the tongue is engaged with the neck to lock and stop the container when the container reaches the final position, wherein the activation unit includes a first biasing member, a needle shield having a first arm and an activator having a costa, the holding unit includes a holder having a bump, the first biasing member abuts against the needle shield and the holder, and the first arm is confined by the bump and the costa to maintain a state that the needle shield protrudes out of the holding unit in a proximal direction, wherein the needle shield further includes a second arm, the activator further includes an ear, the holding unit includes a housing having a first finger, the activator is pushed by the second arm in a distal direction such that the ear is engaged with the first finger when the needle shield is pushed back in the distal direction.

15. The medicament delivery device according to claim 14, wherein the holding unit includes a support having a prong and a first aperture, the housing includes a second finger, a slider includes a first fin, the prong is engaged with the second finger, and the first fin is releasably engaged with the first aperture.

16. The medicament delivery device according to claim 15, wherein the activator includes a lobe, the first fin of the slider includes a web, the driving unit further includes a second biasing member which abuts against the slider and the holding unit, and the first fin is released from the first aperture to allow the slider sliding in the proximal direction by the lobe sliding over the web while the activator is pushed in the distal direction.

17. The medicament delivery device according to claim 14, wherein the needle shield includes a third arm, the holding unit includes a shoulder, and after the activator is pushed in the distal direction, the first arm slides over the bump to allow the needle shield sliding in the proximal direction till the third arm contacts the shoulder.

* * * * *